(12) United States Patent
Nakao

(10) Patent No.: US 7,618,437 B2
(45) Date of Patent: Nov. 17, 2009

(54) ENDOSCOPE RETRIEVAL INSTRUMENT ASSEMBLY

(75) Inventor: Naomi L. Nakao, New York, NY (US)

(73) Assignee: Granit Medical Innovation, LLC, New York, NY (US)

( * ) Notice: Subject to any disclaimer, the term of this patent is extended or adjusted under 35 U.S.C. 154(b) by 425 days.

(21) Appl. No.: 11/182,404

(22) Filed: Jul. 15, 2005

(65) Prior Publication Data

US 2007/0016225 A1 Jan. 18, 2007

(51) Int. Cl.
*A61B 17/26* (2006.01)

(52) U.S. Cl. .................................... 606/213
(58) Field of Classification Search .......... 606/110–115
See application file for complete search history.

(56) References Cited

U.S. PATENT DOCUMENTS

| | | | |
|---|---|---|---|
| 5,147,371 A * | 9/1992 | Washington et al. ........ 606/127 |
| 5,234,439 A | 8/1993 | Wilk et al. |
| 5,279,539 A | 1/1994 | Bohan et al. |
| 5,352,184 A | 10/1994 | Goldberg et al. |
| 5,643,283 A | 7/1997 | Younker |
| 5,741,271 A * | 4/1998 | Nakao et al. ................ 606/114 |
| 5,759,187 A | 6/1998 | Nakao et al. |
| 5,906,621 A | 5/1999 | Secrest et al. |
| 6,814,739 B2 * | 11/2004 | Secrest et al. ............... 606/114 |
| 2003/0004538 A1 | 1/2003 | Secrest et al. |

* cited by examiner

*Primary Examiner*—(Jackie) Tan-Uyen T. Ho
*Assistant Examiner*—Gregory Anderson
(74) *Attorney, Agent, or Firm*—R. Neil Sudol; Henry D. Coleman; William J. Sapone

(57) ABSTRACT

A medical instrument includes an elongate tubular introducer member, an elongate slider member disposed at least partially inside the tubular member, a loop provided at a distal end of the slider member, a pouch connected to the loop so that the loop defines a mouth opening of the pouch and so that the pouch is slidable along at least a proximal portion of the loop, and a tether connected to the pouch at a proximal side thereof. The tether extends into the tubular member and is fastened to the tubular member at a location spaced by a distance from a distal tip of the tubular member. The tether has a length from the fastening location to the pouch that is less than the distance between the location and the tip of the tubular member.

15 Claims, 8 Drawing Sheets

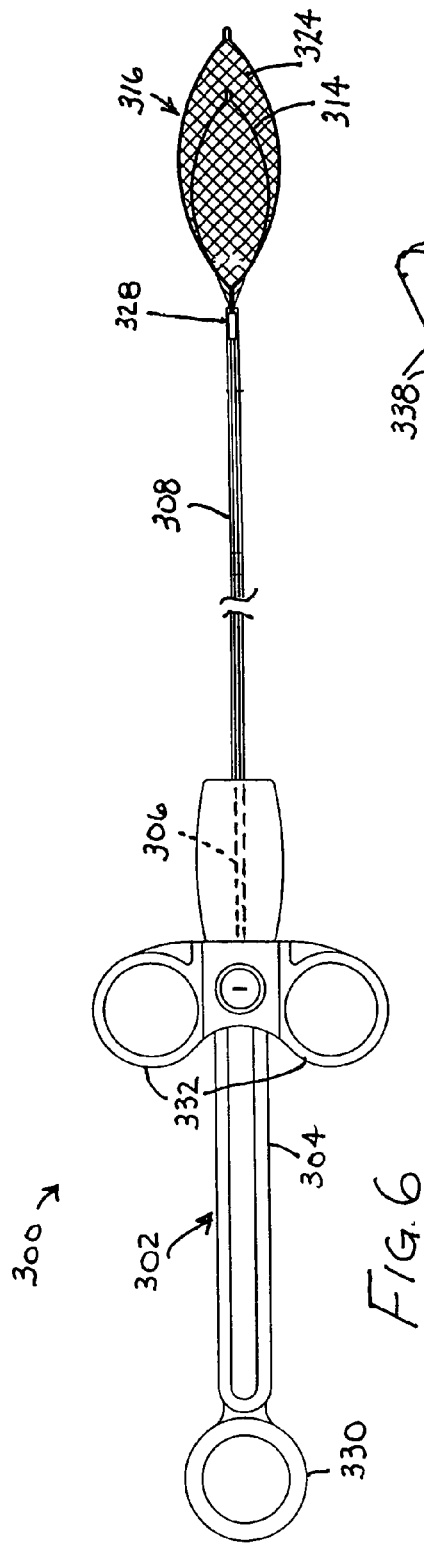
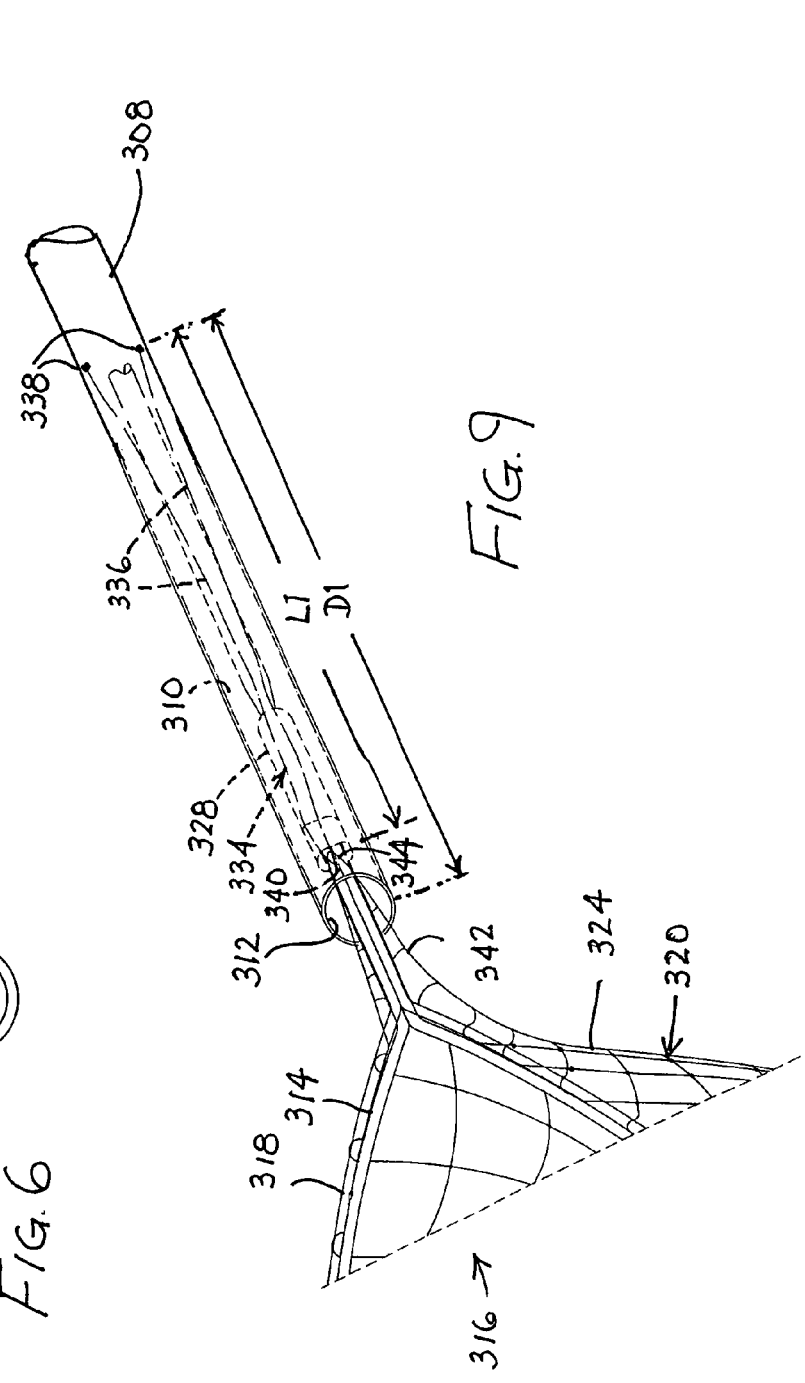
FIG. 6
FIG. 9

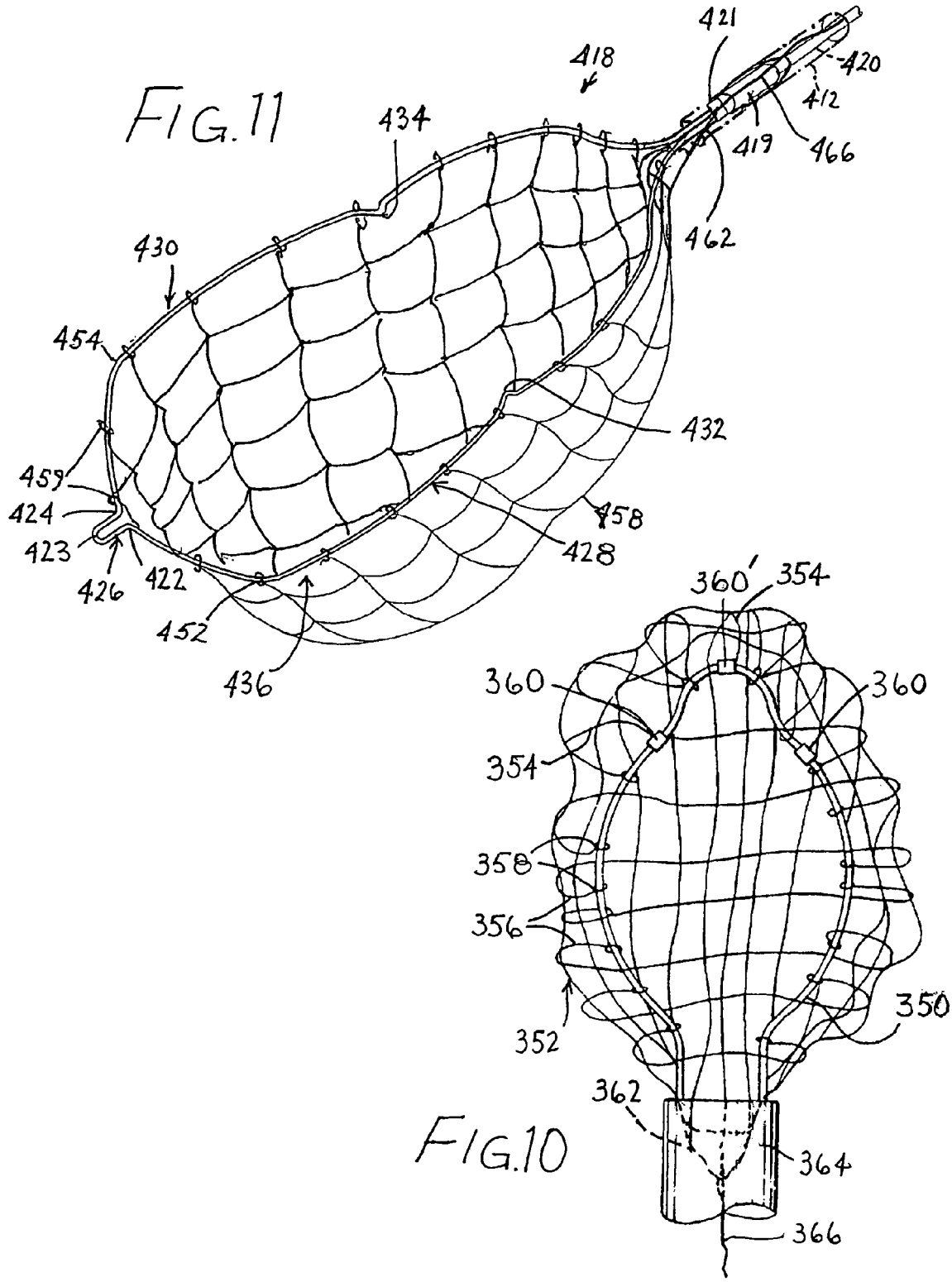

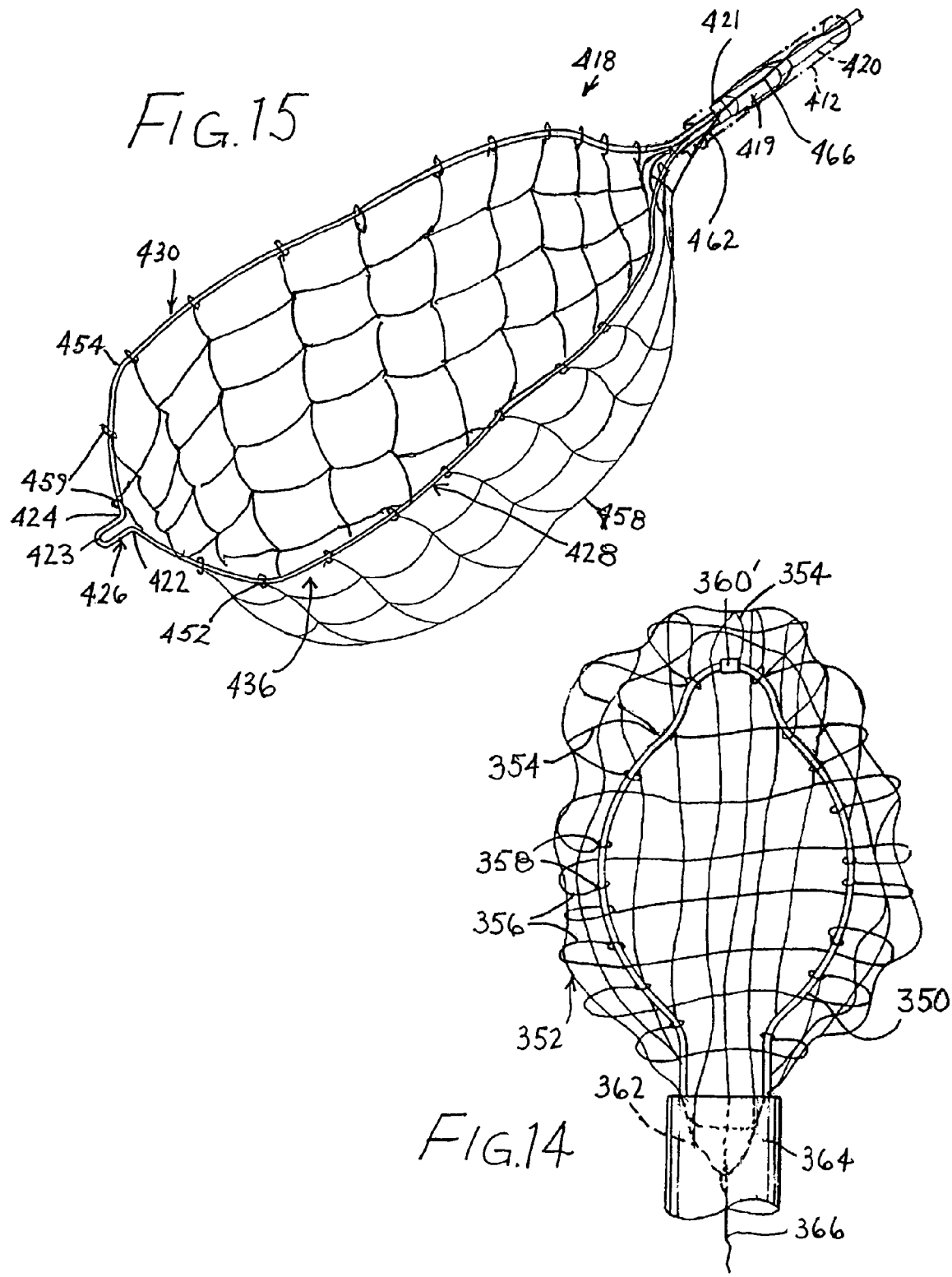

ENDOSCOPE RETRIEVAL INSTRUMENT ASSEMBLY

FIELD OF THE INVENTION

This invention relates to a surgical instrument assembly for use in retrieving objects from internal body cavities. This invention also relates, more specifically, but not exclusively, to a surgical instrument assembly for use in snare cauterization operations.

BACKGROUND OF THE INVENTION

In a conventional endoscopic snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. The use of a forceps generally prevents one from removing more than a biopsy sample from the patient. The forceps naturally tears off a tissue sample from a severed polyp, leaving the main body of the polyp in the patient. In using suction, a vacuum is applied via a suction channel of the endoscope. The use of suction has the drawback of frequently preventing visual inspection of the patient's internal tissues during withdrawal of the endoscope. The polyp or other tissue mass is drawn against the front end of the endoscope, thus obscuring the light source and the observation lens.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In some cases, the endoscope must be removed without the polyp and the patient given an enema in an attempt to flush out the polyp from the colon.

Furthermore, there are numerous cases where a severed polyp is never recovered. Sometimes, the polyp is masticated during the retrieval attempt. In all such cases, the pathologist is unable to determine whether the polyp contains carcinoma in situ (localized to the mucosa) or infiltrative carcinoma (spread beyond the muscularis mucosa layer). The patient must then undergo a colon resection, sometimes unnecessarily.

In any event, the manipulations necessary to remove a severed polyp generally increase the trauma to the patient, the expense of the surgery and the hospitalization time. A number of U.S. patents have disclosed techniques for improving snare cauterization operations to facilitate the capture and retrieval of severed polyps. For instance, pursuant to U.S. Pat. No. 5,201,740 of Nakao et al., snare cauterization operations are performed with a surgical instrument assembly comprising a tubular sheath member carrying a metallic cauterization loop and a metal wire operatively connected to the loop, the wire passing longitudinally through the sheath. An electrical supply is operatively connectable to the wire, while a flexible web member is connected to the loop to form a capture pocket, the loop defining a mouth opening of the pocket. During use of the snare cauterization loop, the web member is passed over and substantially surrounds a polyp. The pocket captures the polyp at the same time that the cauterization loop is energized to effectuate a severing of the polyp.

Other improvements are disclosed in U.S. Pat. Nos. 5,190,542, 5,374,273, 5,234,439, 5,782,840, 5,741,271, 5,336,227, 5,486,182, 5,759,187, and U.S. Patent Publication No. 20050085808 all patents to N. Nakao et al.

OBJECTS OF THE INVENTION

An object of the present invention is to provide an improved endoscopic instrument assembly for the retrieval of polyps and other objects from patients.

A more specific object of the present invention is to provide such an improved instrument assembly that includes snare cauterization capability.

A related object of the present invention is to provide a snare cauterization assembly wherein the capture and retrieval of severed polyps is facilitated.

Another particular object of the present invention is to provide such an instrument assembly which is simple to manufacture and therefore inexpensive.

A further particular object of the present invention is to provide such an instrument assembly which is easy to use.

These and other objects of the invention will be apparent from the drawings and descriptions herein. Although every object of the invention is believed to be attained by at least one embodiment of the invention, there is not necessarily any one embodiment that achieves all of the objects of the invention.

SUMMARY OF THE INVENTION

The present invention is directed chiefly to endoscopic retrieval instruments that are insertable through a working channel of an endoscope and manipulated from outside a patient to capture and remove a tissue mass such as a severed polyp. The retrieval instruments each include a pouch attached to a flexible loop. The severing of the tissue mass may be accomplished by a separate instrument such as a cutting snare. Alternatively, the loop holding the capture pouch may conduct electrical current for implementing the cutting and cauterization of organic tissues.

The separate cutting snare may be a monofilament wire or a thin braided cable that is used to cut small polyps by simply being drawn through base region of the polyp. Such a monofilament wire or thin braided cable need not conduct electrical current since cauterization is not necessary where a polyp is so small as to be vascularized by only capillaries, without a dedicated artery. The separate cutting snare may be electrically energized where larger polyps are to be removed. In such a case, the cauterization will avoid a major gastrointestinal hemorrhage.

A separate cauterization instrument is particularly useful where the tissue mass to be removed from an internal organ is a large sessile polyp, (a polyp that lays flattened against the organ wall). Fluid is injected under the tissue mass to raise it from the organ wall and facilitate removal without perforating the organ. If necessary, removal of the undesirable tissue mass is effectuated piecemeal. In such a case, several attempts at cutting the abnormal tissue are necessary, before retrieval is contemplated. It is therefore necessary to first use a cautery snare without an attached pouch, and only once the entire tumor has been resected, retrieval is initiated by bringing forth a retrieval net.

In contrast, if the tissue mass is pedunculated (has a pedicle or neck region), then it is convenient to use a cauterization snare with a capture pocket attached directly thereto, about the snare loop. Thus, in contrast to the case of a large sessile polyp as described above, a pedunculated polyp may be resected in one maneuver, and therefore it is convenient to use a cautery retrieval device (cautery snare with retrieval net assembly). The instrument is manipulated to place the pouch about the polyp, the catheter is moved forward to partially retract the loop and close the loop about the pedicle, and current is conducted through the loop to sever the tissue mass at the pedicle. The severed polyp or tissue mass remains in the pouch and is withdrawn from the patient, together with the endoscope through which the cautery-retrieval instrument was deployed.

The consistency of a polypoid specimen is similar to the consistency of chicken liver, i.e. very delicate and soft. It is crucial that a specimen remain intact for proper pathologic evaluation, because the presence of malignant cells and their location in the polyp influence the subsequent clinical management of the patient: if the malignant cells invade more deeply than the muscularis mucosa layer, the patient will have to undergo a colon resection. If the cells are confined to the mucosal layer (the outer layer of the polyp) then removal of the polyp (polypectomy) is sufficient. In addition, if the polyp has a stalk or pedicle and there is invasion of malignant cells into the pedicle, that is considered invasive carcinoma and a colon resection is indicated. If the stalk is clear of malignant cells, a mere polypectomy is sufficient. The presence of the tether, and its special configuration vis-à-vis the netting and the snare secure the preservation of the specimen for proper analysis in the following fashion: When the polyp is engulfed, either before cautery or after resection, the tether allows the net to slide up the snare in order to form a soft, roomy pouch in which to gently nestle the specimen. If the physician feels that the polyp or specimen has not been properly surrounded, the loop may be re-opened, allowing the net to slide back into its position, evenly distributed around the open mouth of the snare. When proper capturing of the polypoid lesion or specimen is achieved, the snare is again tightened, and the pouch slides distally on the closing snare for final secure specimen retrieval. The endoscope is then withdrawn with the specimen inside the pouch held securely in view for the endoscopist. This allows visualization of the specimen as it is being withdrawn from the body, as well as examination of the organ lumen on the way out.

A medical instrument in accordance with the present invention comprises an elongate tubular introducer member, an elongate slider member disposed at least partially inside the tubular member, a loop provided at a distal end of the slider member, a pouch connected to the loop so that the loop defines a mouth opening of the pouch and so that the pouch is slidable along at least a proximal portion of the loop, and at least one tether connected to the pouch at a proximal side thereof. The tether extends into the tubular member and is fastened to the tubular member at a location spaced by a distance from a distal tip of the tubular member. The tether has a length from the fastening location to the pouch that is less than the distance between the location and the tip of the tubular member.

The instrument of the present invention is particularly suitable for endoscopic interventions. Thus, the tubular member may have a transverse dimension suitable for insertion of the instrument through a working channel of a rigid or flexible endoscope.

Pursuant to another feature of the present invention, the slider member is connectable at a proximal end to a source of electrical current, the loop being made of a conductive material. In this case, the pouch is provided as part of a cauterization snare assembly.

Alternatively, as indicated above, the pouch member may be a separate instrument that is used for tissue retrieval purposes either alone or in conjunction with a cauterization snare. The cauterization snare and the pouch member may be deployed via respective channels or lumens of the tubular introducer member.

In another embodiment of the invention, a tissue retrieval assembly has two loops, a cauterization loop and a retrieval pouch loop, that are connected to one another. In at least one embodiment, the cauterization snare is smaller than and nested inside the retrieval pouch loop. The slider member is connectable at a proximal end to a source of electrical current to conduct current through the smaller loop, the cauterization snare. The snare and the retrieval pouch loop may be separate along their entire lengths and connected to one another only at their stems, proximal of their loop-shaped body portions. Alternatively, the snare and the retrieval pouch loop mare share a distal end portion.

The pouch may be a net element. In that case, a distal portion of the tether may be interwoven with strands of the net. In this case, the forces exerted by the tether on the pouch are distributed along a portion of the portion at the proximal side thereof. Also, the extension of the tether along the pouch enhances the coupling of the tether to the pouch and serves in part to maintain the open configuration of the pouch.

An endoscopic surgical device for retrieving severed tissue from within a patient's body comprises, in accordance with the present invention, a support unit, a tissue retrieving net system, and a net controller. The support unit comprises a body defining a passage therethrough and an elongated introducer member having a first end section proximal and fixed with respect to the body and a second end section remote from the body. The introducer member defines a passage aligned with the body passage and opening at the second end section. The tissue retrieving net system includes a net comprising a wire-like resilient loop and a net element having a mouth section slidably disposed on the loop and a tissue receiving pouch section, the net disposed adjacent the second end for deployment and retrieval through the introducer passage opening. The tissue retrieving net system further includes a net deployment and retrieval assembly extending substantially through the introducer passage and connected to the net, the assembly comprising a motion transmitting member extending in the introducer passage to the loop. The tissue retrieving net system also includes a net actuator unit comprising a first handle fixed with respect to the body and a second handle fixed with respect to the motion transmitting member and movable relative to the first handle so that shifting the second handle relative to the first handle shifts the net into and out of the introducer passage opening. The introducer member passage has a diametrical extent substantially smaller than the width of the loop when the loop is deployed.

The introducer member engages the loop at the opening and resiliently collapses and elongates the loop as the net is retrieved and moves into the introducer member passage, the loop resiliently returning to an uncollapsed configuration as the net system is deployed. The net controller assures that the net mouth extends fully about the loop when the loop is deployed and comprises a net tether having one end anchored within the introducer member passage a given distance from the second introducer member end section equal to at least half the length of the loop in an collapsed condition, an opposite end secured to the net mouth, and a free length less than the given distance. The tether assures full net mouth opening when the net is deployed while permitting the mouth to be closed when tissue is disposed in the net pouch and the loop is retrieved.

The tether's length being shorter than the distance between the distal tip of the tubular introducer member and the point of attachment of the tether to the introducer member enables a portion of the net to be brought inside the tubular member. This structure stretches the net to produce a tauter, flatter net configuration while still maintaining the advantage of forming a pouch when the retrieval member is withdrawn. A tauter, flatter net configuration particularly in the fully extended position of the net element or tissue retrieval system assists in tissue handling procedures. Without the shorter tether, the net may create an impediment to proper visualization of a polypoid lesion because of the pouchiness of the netting. The shorter tether enhances visibility, and the manipulating of the loop with the net element is facilitated. Thus, the important function of the tether, to provide for a lax pouch when the snare is tightened upon the polyp, is preserved. But when pouchiness of the net is undesirable, i.e. during the initial part of the specimen capture operation, the net is flat and only minimally visible, allowing for maximum freedom in manipulation. In addition, there is a more reliable connection of the tether to the net, inasmuch as the tether and the proximal net portion are shielded from damage inside the tubular introducer member.

A medical tissue retrieval instrument in accordance with the present invention includes a pouch attached to a flexible loop. Before initiation of a retrieval procedure, the pouch and the loop are positioned inside an elongate tubular member such as a catheter. An elongate slider member is disposed at least partially inside the tubular member and is connected to the loop for moving the loop and the pouch out of the catheter and about a tissue mass such as a polyp. The pouch is fixed to the loop at least at a distal end and a proximal end of the loop, and possible along the entire loop. The pouch is made of a flexible net material with fine strands or threads. Preferably, the pouch is woven in a warp knitting fashion whereby each eye is knotted at the corners, as is done in a hairnet. Thus, the small squares that are created have a knot at each corner. This method, in contrast to weft knitting whereby the threads are woven by crossing one another and can freely slide in any direction, assures a permanence in size and configuration of the squares. It is important for endoscopic retrieval procedures that the small squares that are defined by the fine threads of the netting are not too large, so as not to permit loss of tissue, and yet are not too close to one another, so as not to create a density of the netting that would not permit proper visualization of the polyp. The optimal netting for an endoscopic retrieval pouch as described herein has squares with 6-8 mm sides, co-joined by the warp knitting method. It is possible to accomplish the same result by forming three, five or more sided constructions with the weft knitting method. In some cases there are two threads to a side of the square or other minimal unit of the net. The most important aspect in every case is that the eyes are affixed in a way that does not permit random sliding or other type of movements of the individual threads. The pouch is sufficiently fine so that a proximal end of the pouch is retractable into the tubular member while the pouch holds a tissue mass. The pouch is sufficiently flexible to expand out to engulf a large tissue mass while a proximal end of the pouch is retracted into the tubular member. This is accomplished by selecting such fine thread for the nets, that when wet, the net virtually disappears in the digestive juices, especially when held flat during the capturing operation, as facilitated by the shorter tether.

BRIEF DESCRIPTION OF THE DRAWING

FIG. 6 is a schematic top or plan view of a snare cauterization and retrieval assembly in accordance with the present invention, showing a cauterization snare and a retrieval basket including a wire loop with a retrieval pouch made of netting material.

FIG. 9 is a schematic perspective view on an even larger scale, showing the pouch extending into a tubular member and a tether connected to the pouch inside the tubular member.

FIG. 10 is a partial schematic top or plan view of a surgical retrieval device in accordance with the present invention.

FIG. 11 is a partial schematic perspective view of a further surgical retrieval device in accordance with the present invention.

FIG. 14 is a partial schematic top or plan view of the surgical retrieval device of FIG. 10 with some modifications.

FIG. 15 is a partial schematic top or plan view of the surgical retrieval device of FIG. 11 with some modifications.

DETAILED DESCRIPTION

The drawings illustrate a number of different medical retrieval devices, all having a net element forming a pouch where the net element may be at least partially slidably secured along a wire loop, particularly along a proximal end portion of the loop, facing the user of the instrument. The wire loop and the pouch are secured to a distal end of a wire pusher that extends through a tubular introducer member (e.g., catheter) transmits axial motion to the loop and net element. At the onset of an endoscopic procedure the wire loop and the pouch or net element are completely housed in a tubular introducer member such as a catheter. The catheter is inserted into a patient via a working channel of an endoscope. When the distal end of the endoscope has reached a surgical or diagnostic site inside the patient, such as a polyp in the colon, the wire loop and the net element or pouch are ejected from the catheter. The wire loop automatically opens to form a mouth of the pouch and is manipulated from outside the patient to place the net element over a tissue mass such as a polyp. During the course of a polyp capture operation, the loop may be partially retracted into the catheter. If the net element is slidably secured to the loop, the loops slides relative to the net element at the distal tip of the catheter, as the loop is retracted into the catheter, the net element remaining for the most part outside the catheter. A tether is attached to the net element, on the proximal side thereof, for ensuring that the net element or pouch is fully opened when the loop is pushed out of the catheter after having been partially pulled into the catheter.

Figure 1:
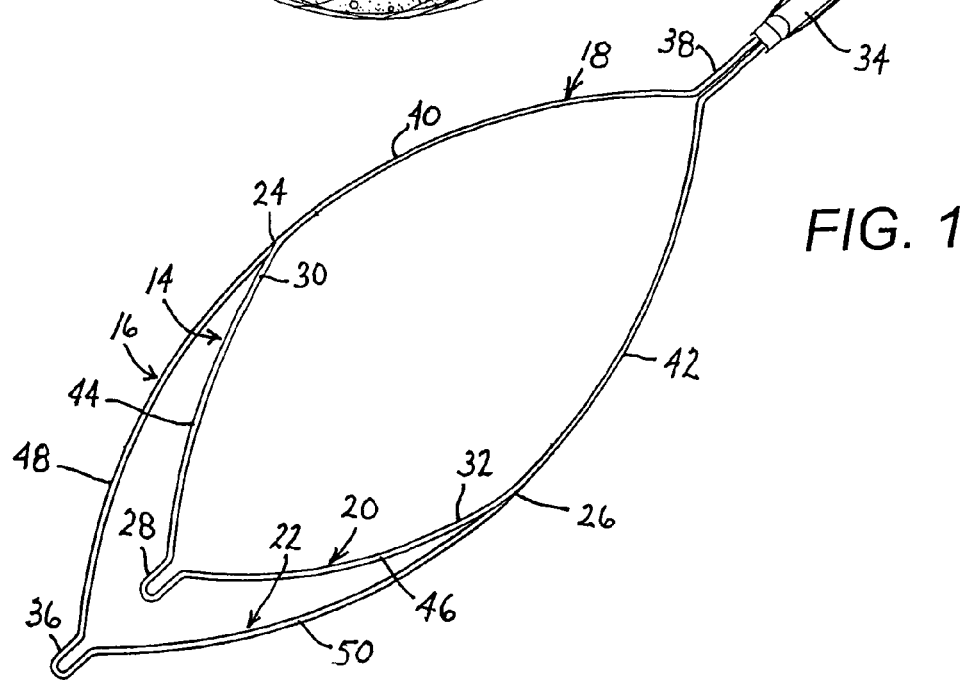
FIG. 1 is a schematic perspective view of a two-tiered cauterization loop.

As depicted in FIG. 1, a surgical instrument for use in an endoscopic tissue resection procedure comprises an elongate electrically conductive slider member or pusher wire 10 movably extending through a tubular introducer member 12 such as a catheter. The catheter is dimensioned to fit down the biopsy channel of a flexible endoscope. The instrument of FIG. 1 additionally comprises an inner loop 14 and an outer loop 16 both operatively connected to a distal end of wire 10. Inner loop 14 and the outer loop 16 have a common proximal loop portion 18 and different distal loop portions 20 and 22. The distal loop portion 22 of outer loop 16 is longer than the distal loop portion 20 of inner loop 14 with the result that the outer loop is larger than the inner loop.

At its proximal end (not shown), wire 10 is operatively connectable to a voltage source (not shown) for purposes of conducting current through inner loop 14. Distal loop portion 22 of outer loop 16 is preferably provided with a coating of electrically insulating material such as heat-shrunk polytetrafluoroethylene, so that current is not conducted through distal loop portion 22 in the event of accidental contact with organic tissues during an endoscopic resection procedure.

Inner loop 14 and outer loop 16 are coplanar with one another at least along their proximal sides. Distal loop portions 20 and 22 are soldered, glued, ultrasonically welded, laser welded or otherwise attached to one another at junctions 24 and 26, on their proximal side.

Distal loop portion 20 of inner loop 14 is continuous and integrally formed with proximal loop portion 18 so that inner loop 14 may be viewed as the main loop. Inner loop has a nose 28 at a distal end and a pair of mirror image wire sections or segments 30 and 32 extending between the nose at the distal side and a crimping connector 34 at the proximal side. Distal loop portion 22 of outer loop 16 comprises a separate wire section soldered, glued, ultrasonically welded, coupled by laser, or otherwise attached to inner loop 14 along opposite sections 30 and 32 thereof. Distal loop portion 22 itself has a nose 36 generally aligned with nose 28 and crimping connector 34. Distal loop portion 22 of outer loop 16 is soldered, glued, ultrasonically welded, laser welded or otherwise attached to the opposite sections 30 and 32 of inner loop 14 preferably at points equidistant from nose 28 (and also equidistant from connector 34).

Proximal loop portion 18 is connected along a middle region 38 to wire 10 by means of connector 34. Proximal loop portion 18 is concave in a direction facing away from wire 10 and convex on a side facing the wire. Proximal loop portion 18 has a pair of first arms 40 and 42 each continuous and contiguous with the middle region 38 and extending away from the middle region, wire 10 and from each other. Distal loop portion 20 of inner loop 14 is concave in a direction facing wire 10 and convex on a side facing away from the wire. Distal loop portion 20 has a pair of arms 44 and 46 continuous and contiguous with arms 40 and 42 of proximal loop portion 18 so that distal loop portion 20 forms inner loop 14 with proximal loop portion 18. Distal loop portion 22 of outer loop 16 is also concave in a direction facing wire 10 and convex on a side facing away from the wire. Distal loop portion 22 has a pair of arms 48 and 50 each continuous and contiguous with respective arms 42 and 44 of proximal loop portion 18 so that the outer distal loop portion 22 together with proximal loop portion 18 forms outer loop 16 as a continuous and closed loop.

Figure 2:
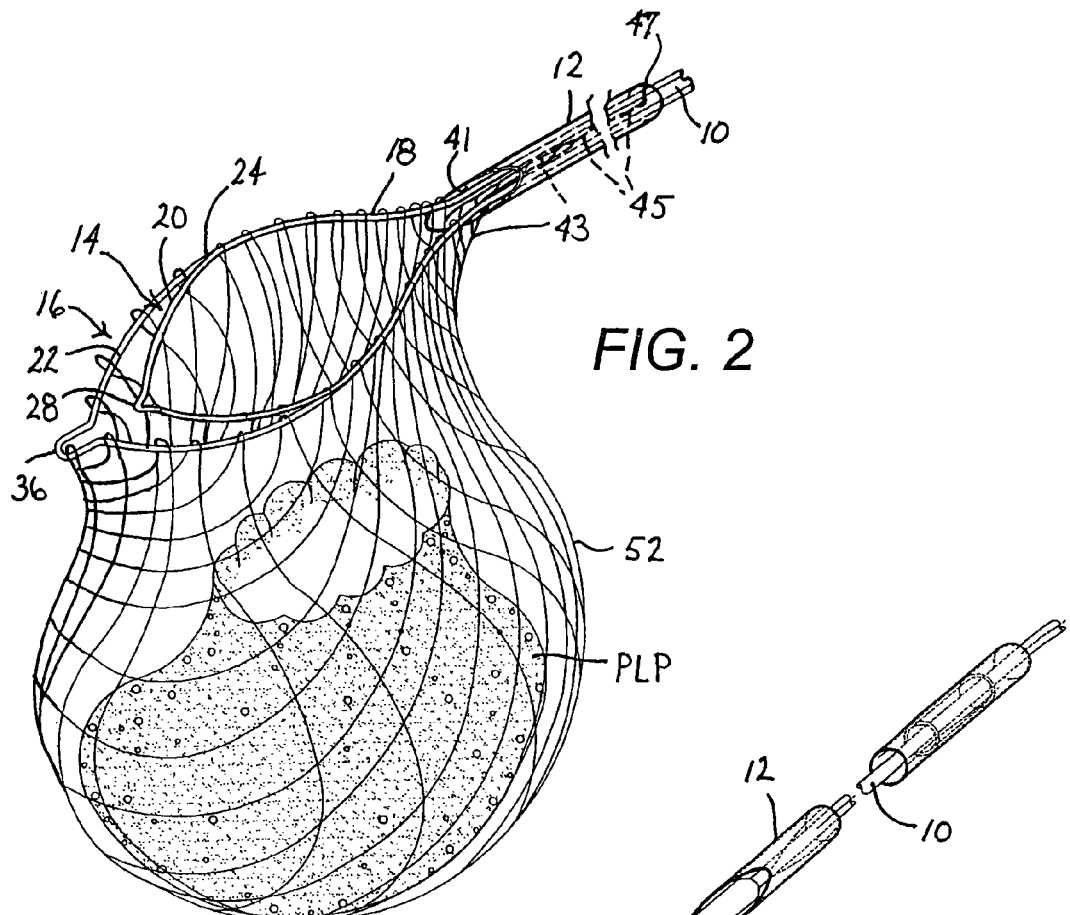
FIG. 2 is a schematic perspective view of the cauterization loop of FIG. 1, with the addition of a retrieval net or pouch.

As illustrated in FIG. 2, outer loop 16 may be provided with a netting or net element 52 that defines a pouch or tissue capture pocket. More specifically, net element 52 is attached to proximal loop portion 18 and outer distal loop portion 22 to form a pouch with outer loop 16 defining a mouth of the pouch. In the device or instrument of FIG. 2, inner loop 14 functions as a cauterization snare while outer loop 16 functions as a retrieval basket. Because current is conducted through inner distal loop portion 20 rather than outer distal loop portion 22 during a tissue severing and cauterization procedure, net element 52 will remain attached to outer loop 16 to facilitate the harvesting of multiple polyps from a patient with the same instrument.

Net element 52 may be slidably attached to outer loop 16 at least along a proximal side thereof. Slidability facilitates repeated withdrawal and extension of loops 14 and 16 by enabling net element 52 to remain outside tubular member 12 during a retraction stroke of wire 10. The net bunches at a distally located mouth 41 of tubular member 12 during a generally partially retraction or withdrawal of loops 14 and 16 into the tubular member. Preferably, net element 52 is fixed to outer loop 16 at a distal point, for example, along nose 36, to prevent the displacement of the net element to one side or the other of the outer loop 16. Fixation may be accomplished by any suitable method, including a clamp 360' (see FIG. 10), a ringlet, or a glob of biocompatible adhesive.

Particularly in the case that net element 52 is slidably secured to outer loop 16 along at least a proximal portion thereof, net element 52 includes a proximal end portion 43 that extends through mouth 41 into tubular member 12. Portion 43 remains in part inside tubular member at all times during a snare retrieval procedure. One or more tether lines 45 are attached on one side to proximal net portion 43 and are fastened on an opposite side the tubular member 12 at one or more anchor points 47. Each tether line 45 necessarily has an effective length that is significantly less than the distance between anchor point 47 and mouth opening 41 at the free end or distal tip of tubular member 12. Tether 41 exerts a restraining influence on net element 52 via proximal net portion 43, thereby ensuring that net element 43 extends essentially fully around outer loop 16 upon a complete ejection of loops 14 and 16 from tubular member 12. Anchor point 47 and the length of tether 45 are selected to enable a complete retraction of loops 14 and 16 and net element 52 into tubular member 12 during insertion into the working or biopsy channel of the endoscope.

Figure 3:
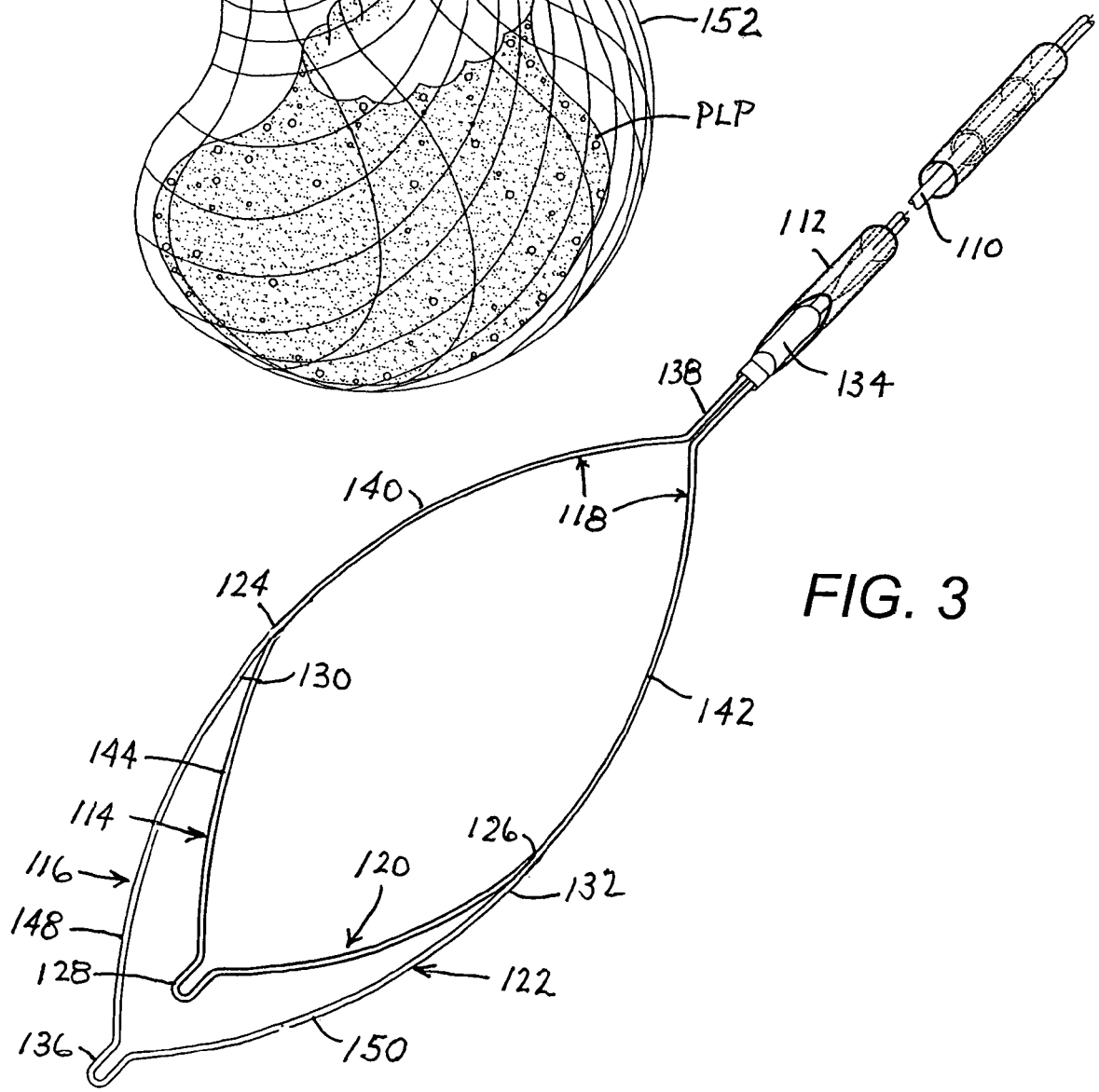
FIG. 3 is a schematic perspective view of another two-tiered cauterization loop.

As illustrated in FIG. 3, a modified surgical instrument for use in an endoscopic tissue resection procedure comprises an elongate electrically conductive wire 110 extending through a tubular member 112 with an outer diameter (not designated) smaller than the diameter of an endoscope biopsy channel. The distal end of wire 110 is provided an inner loop 114 and an outer loop 116 which have a common proximal loop portion 118 and different distal loop portions 120 and 122. Outer distal loop portion 122 is longer than inner distal loop portion 120 so that outer loop 116 is larger than inner loop 114.

At its proximal end (not shown), wire 110 is operatively connectable to an electrical power supply (not shown) for purposes of applying a voltage across inner loop 114. Distal loop portion 122 of outer loop 116 is preferably provided with a coating of electrically insulating material such as heat-shrunk polytetrafluorethylene, so that current is not conducted through distal loop portion 122 during an endoscopic resection procedure.

Inner loop 114 and outer loop 116 are coplanar with one another along proximal loop portion 118. Inner and outer distal loop portions 120 and 122 are soldered, glued, ultrasonically welded, laser welded or otherwise attached to one another at junctions or joints 124 and 126, on their proximal side.

Outer distal loop portion 122 is continuous and integrally formed with proximal loop portion 118 so that outer loop 116 may be viewed as the main loop. Outer loop 116 has a nose 128 at a distal end and a pair of mirror image wire sections or segments 130 and 132 extending between the nose at the distal side and a crimping connector 134 at the proximal side. Distal loop portion 120 of inner loop 114 comprises a separate wire section soldered, glued, ultrasonically welded, laser welded or otherwise attached to outer loop 116 along opposite sections 130 and 132 thereof. Distal loop portion 120 itself has a nose 136 generally aligned with nose 128 and crimping connector 134. Distal loop portion 120 of inner loop 114 is soldered, glued, ultrasonically welded, laser welded or otherwise attached to the opposite sections 130 and 132 of outer loop 116 preferably at points equidistant from nose 128 (and also equidistant from connector 134).

Proximal loop portion 118 is connected along a middle region 138 to wire 110 by means of connector 134. Proximal loop portion 118 is concave in a direction facing away from wire 110 and convex on a side facing the wire. Proximal loop portion 118 has a pair of first arms 140 and 142 each continuous and contiguous with the middle region 138 and extending away from the middle region, wire 10 and from each other. Distal loop portion 120 of inner loop 114 is concave in a direction facing wire 110 and convex on a side facing away from the wire. Distal loop portion 120 has a pair of arms 144 and 146 continuous and contiguous with arms 140 and 142 of proximal loop portion 118 so that distal loop portion 120 together with proximal loop portion 118 forms inner loop 114. Distal loop portion 122 of outer loop 116 is also concave in a direction facing wire 110 and convex on a side facing away from the wire. Distal loop portion 122 has a pair of arms 148 and 150 each continuous and contiguous with respective arms 142 and 144 of proximal loop portion 118 so that the outer distal loop portion 122 together with proximal loop portion 118 forms outer loop 116 as a continuous and closed loop.

Figure 4:
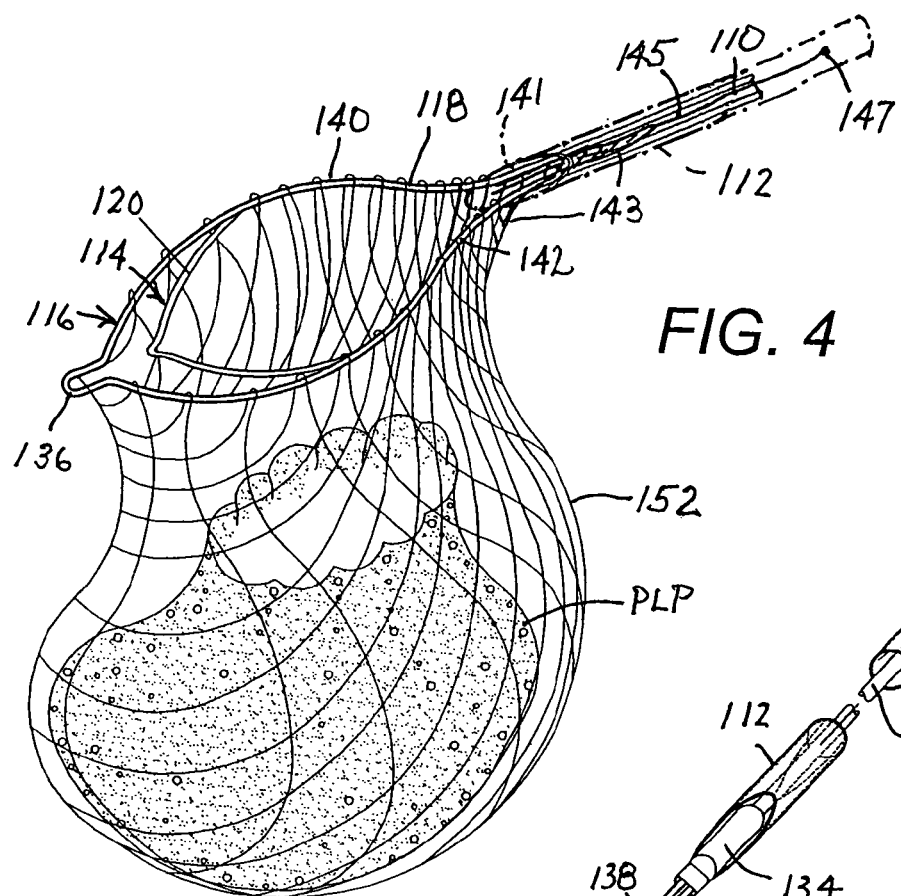
FIG. 4 is a schematic perspective view of the cauterization loop of FIG. 3, with the addition of a retrieval net or pouch.

As illustrated in FIG. 4, outer loop 116 may be provided with a netting or net element 152 that defines a pouch or tissue capture pocket. More specifically, net element 152 is attached to proximal loop portion 118 and outer distal loop portion 122 to form a pouch with outer loop 116 defining a mouth of the pouch. In the device or instrument of FIG. 4, inner loop 114 functions as a cauterization snare while outer loop 116 functions as a retrieval basket. Because current is conducted through inner distal loop portion 120 and not through outer distal loop portion 122 during a tissue severing and cauterization procedure, net element 152 will remain attached to outer loop 116, thereby facilitating the harvesting of multiple polyps from a patient with the same instrument.

Net element 152 may be slidably attached to outer loop 116 at least along a proximal side thereof. Slidability facilitates repeated withdrawal and extension of loops 114 and 116 by enabling net element 152 to remain outside tubular member 112 during a retraction stroke of wire 110. The net bunches at a distally located mouth 141 of tubular member 112 during a generally partially retraction or withdrawal of loops 114 and 116 into the tubular member.

Particularly in the case that net element 152 is slidably secured to outer loop 116 along at least a proximal portion thereof, net element 152 includes a proximal end portion 143 that extends through mouth 141 into tubular member 112. Portion 143 remains in part inside tubular member at all times during a snare retrieval procedure. One or more tether lines 145 are attached on one side to proximal net portion 143 and are fastened on an opposite side the tubular member 112 at one or more anchor points 147. Each tether line 145 necessarily has an effective length that is less than the distance between anchor point 147 and mouth opening 141 at the free end or distal tip of tubular member 112. Tether 141 exerts a restraining influence on net element 152 via proximal net portion 143, thereby ensuring that net element 143 extends essentially fully around outer loop 116 upon a complete ejection of loops 114 and 116 from tubular member 112. Anchor point 147 and the length of tether 45 are selected to enable a complete retraction of loops 114 and 116 and net element 152 into tubular member 112 during insertion into the working channel of the endoscope.

Providing net elements or pouches 52 and 152 with proximal net portions 43 and 143 that extend into the tubular members 12 and 112 and that are connected to tethers 45 and 145 inside the tubular members provides some distinct advantages over tissue retrieval instruments where the net remains substantially completely outside the tubular member during repeated ejection and retraction operations. The fact that tethers 45, 145 are shorter than the distance between the distal tip of the tubular introducer member 12, 112 and attachment points 47, 147 enables proximal net portion 43, 143 to be brought inside tubular member 12, 112. The net 52, 152 is thereby stretched to produce a tauter, flatter net configuration when the snare assembly is fully deployed, while still maintaining the advantage of forming a pouch when withdrawn. A tauter, flatter net configuration particularly in the fully extended position of the net element 52, 152 assists in tissue handling procedures. Visibility is enhanced and loop handling is facilitated.

Figure 5:
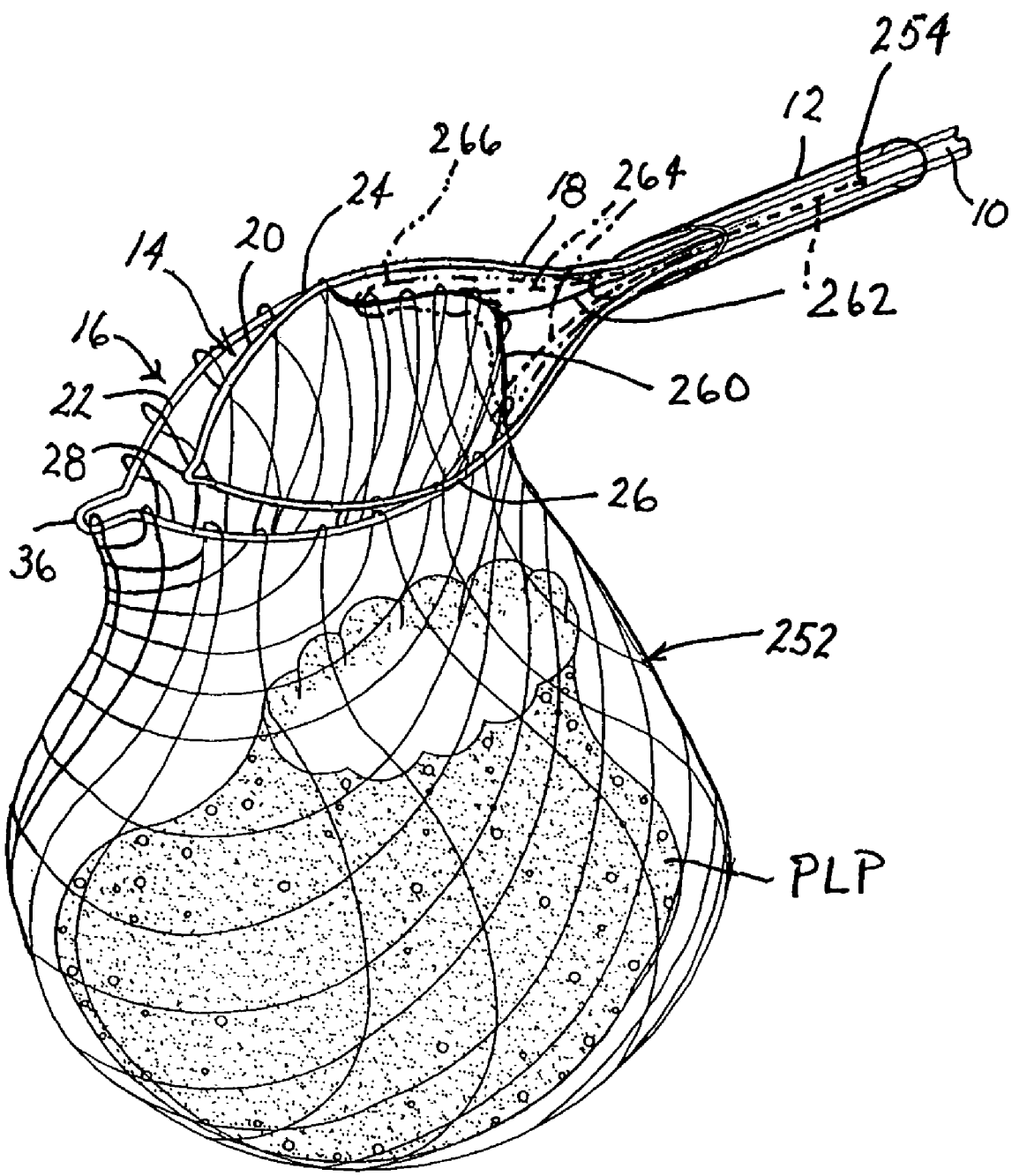
FIG. 5 is a schematic perspective view of a modification of the pouch of FIG. 2, in accordance with the present invention.

FIG. 5 illustrates a modification of the surgical instrument of FIG. 2. Instrument parts in FIG. 5 are designated with the same reference numerals as the same parts in FIG. 2. As depicted in FIG. 5, a pouch 252 made of film or netting material is slidably attached to outer distal loop portion 22 so that the outer loop portion partially defines a mouth (not separately labeled) of the pouch.

Outer loop portion 22 is connected to inner loop portion 20 and to proximal loop portion 18 at junctions or branch points 24 and 26. On a proximal side 258, pouch 252 has a mouth edge or thread 260 that extends between junction or branch point 24 and junction or branch point 26. A tether 262 in the form of a thread is connected at a distal end to the proximal edge or mouth 260 of pouch 252 and extends proximally into tubular member 12 to be connected at a proximal end to tubular member 12 at a point 254 inside the lumen of the tubular member. When the loop assembly, including proximal loop portion 18, inner loop portion 20, and outer loop portion 22, is fully extended in the distal direction, tether 262 pulls edge 260 in the proximal direction to maximize the size or cross-sectional area of the pouch mouth. Plural tethers 264 may be alternatively or additionally provided, tethers 264 being attached to edge 260 at spaced locations therealong, thereby facilitating that the pouch mouth is rounder and wider on the proximal side. Alternatively, a tether 266 may be looped or woven with pouch 252 substantially parallel to or along edge 260. The woven coupling of tether 266 and pouch 252 enhances the reliability of the connection and spreads the forces out over a larger portion of the net. In addition, the woven coupling ensures a greater degree of opening of the pouch, at least along a proximal side thereof.

Tethers 262, 264, 266 necessarily have effective lengths that are significantly greater than the distance between anchor point 254 and the free end or distal tip of tubular member 12.

Tethers 262, 264, 266 serve in part to reopen pouch 252 after the loops 14 and 16 have been retracted inside tubular member 12 during an endoscopic procedure. In other words, tethers 262, 264, 266 serve the additional function of holding the net element when loops 14 and 16 are pushed in the distal direction, thus ensuring that pouch 252 slides relative to the outer loop 16 and has a mouth (not separately labeled) that is open for the capture of a polyp or other tissue mass.

The pouch configuration of FIG. 5 may be used alternatively to net element 152 in the instrument assembly of FIG. 4.

The embodiment of FIG. 5 may be modified so that pouch 252 includes a proximal portion that extends into tubular member 12. In that case, a tether (replacing tether 262) has an effective length that is less than the distance between anchor point 254 and the free end or distal tip of tubular member 12. Tethers 264 in this modified embodiment extend outside tubular member 12 and thus retain an effective length that is greater than the distance between anchor point 254 and the free end or distal tip of tubular member 12.

Distal portions 22 and 122 of loops 16 and 116 may be provided with an electrically insulating coating such as a heat-shrink polytetrafluoroethylene layer. However, the insulating coating on distal portions 22 and 122 of outer loops 16 and 116 is merely a precautionary measure, provided in the event of accidental contact with organic tissues. In the absence of such accidental contact, current will never be conducted via distal loop portions 22 and 122 of outer loops 16 and 116. In contrast, distal portions 20 and 120 of loops 14 and 114 are naked metal, permitting the conducting of current upon contact of the distal portions 20 and 120 with organic tissues inside a patient.

Distal portion 20 (or 120) of inner loop 14 (or 114) may diverge out of the plane of outer loop 16 (or 116), in a direction away from the pouch 52 (or 152). This configuration reduces the likelihood that pouches 52 and 152 will become snagged on the noses 28 and 128 of inner loops 14 and 114, particularly during a deployment process. As the pouches 52 and 152 are drawn into the catheters 12 and 112, the distal portions 20 and 120 of the inner loops 14 and 114 are drawn towards the plane of the outer loops 16 and 116. Loops 14 and 114, particularly distal loop portions 20 and 120, may be made of a stainless steel or other material that has an inherent spring bias tending to reform the distal loop portions into a diverging configuration even upon repeated ejections of the loops 14, 16, 114, 116 from the tubular catheter members 12, 112.

In one extreme embodiment of the multi-tier cutting (and retrieving) snare instruments disclosed herein, proximal loop portion 18 or 118 is much smaller than distal loop portions 20, 22 or 120, 122. Net or pouch 52, 152, 252 can be slidably attached to distal loop portion 22 or 122 so as to be slidable along the major portion of outer loop 16 or 116.

In another extreme embodiment of the multi-tier cutting (and retrieving) snare instruments disclosed herein, proximal loop portion 18 or 118 is much larger than distal loop portions 20, 22 or 120, 122. In this embodiment net or pouch 52, 152 is fixedly attached to outer loop 16, 116 and is therefore not slidable therealong. The net 52, 152 is made sufficiently large and with fine threads so that a large portion of the net remains outside the tubular member 12, 112 when the snare loops are retracted back inside the tubular member, for instance, for purposes of severing a polyp. Tethers as described hereinabove are omitted in the case of net fixation to outer loop 16 or 116.

FIGS. 6-9 depict an endoscopic surgical device 300 for severing and retrieving severed tissue from within a patient's body. Device 300 comprises a support unit 302 including a handgrip body 304 defining a passage 306 therethrough and further including an elongated tubular introducer member 308 having a proximal end section fixed to handgrip body 304 and a distal end section remote from the handgrip body. The tubular introducer member 308 defines a passage 310 aligned with passage 306 in handgrip body 304 and an opening 312 at a distal end of at the distal end section.

Endoscopic device 300 additionally comprises a cauterization snare 314 operatively connectable to a source of electrical current for cutting through and cauterizing internal body tissues such as intestinal polyps. Device 300 also comprises a tissue retrieving net system 316 including a wire-like resilient loop 318 and a net element 320 having a mouth section 322 slidably disposed on the loop and a tissue receiving pouch section 324. Net element 320 is disposed adjacent the distal tip of tubular introducer member 308 for deployment and retrieval through the introducer passage opening 312. A net deployment and retrieval assembly particularly including a wire 326 extends substantially through the introducer passage or lumen 310 and is connected to the net loop 318 and to cauterization snare 314. Wire 326 serves in part to conduct electrical current to cauterization snare 314 and in part as a motion transmitting member for controllably moving cauterization snare 14 and net loop 318 alternately out of and into introducer passage or lumen 310 via opening 312.

Cauterization snare 314 is smaller than and generally coplanar with net loop 318 and may be fixed to loop 318 on a proximal side thereof. Loop 318 may be electrically connected to motion-transmitting wire 326, and thus to cauterization snare 314. However, in practice, current is conducted only through snare 314 inasmuch as loop 318 generally does not come into contact with organic tissues. In an alternative embodiment, loop 318 may be electrically insulated from wire 326 and snare 314. For instance, loop 318 may be provided with a coating of nonconductive or electrically insulating material such as heat-shrunk polytetrafluorethylene. In any event, loop 318 is clamped to snare 314 and wire 326 via a crimping element 328. Crimping element 328 is located along stems (not designated) of snare 314 and loop 318 so that the snare and the loop are separate along their main loop-shaped portions.

Figure 8:
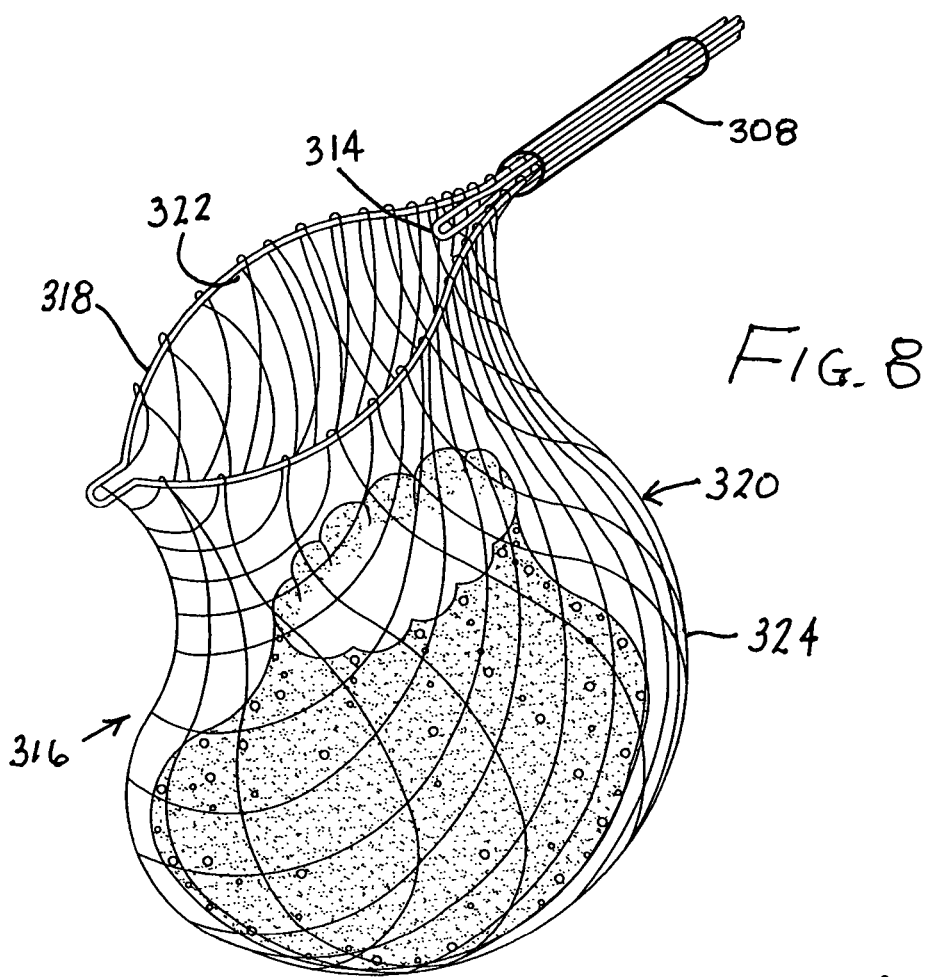
FIG. 8 is a schematic perspective view similar to FIG. 7, showing the cauterization snare in a partially retracted position and a severed polyp in the pouch.
Figure 7:
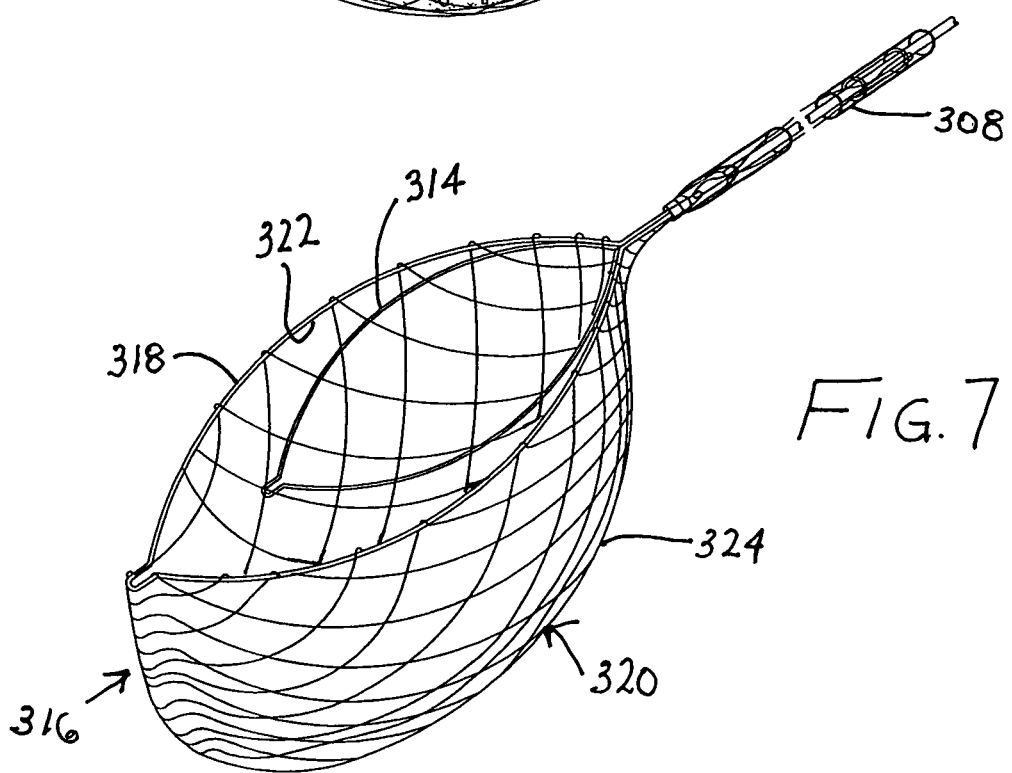
FIG. 7 is a schematic perspective view, on a larger scale, of the cauterization snare and a retrieval basket of FIG. 6.

In another alternative configuration, snare 314 and net system 316 may be independently slidable along an axis of tubular introducer member 308. FIG. 8 shows cauterization snare retracted into passage or lumen 310 and net system 316 extended. A polyp PLP is held inside pouch section 324 after severing of the polyp by cauterization snare 314.

In use, snare 314 and net system 316 are ejected together from tubular introducer member 308 via opening 312. The cauterization snare 314 with the net system 316 is manipulated from outside the patient to place the snare about the neck of a polyp. Snare 314 is then retracted back into tubular introducer member 308 via opening 312, thereby first closing the cauterization loop about the neck of the polyp and then cutting through the neck. The severed polyp PLP becomes enclosed in pouch section 324.

Endoscopic device 300 further comprises a net actuator unit (not separately labeled) including a first handle ring 330 fixed with respect to handgrip body 304 and a pair of second handle rings 332 fixed with respect to the motion transmitting member or wire 326 and movable relative to the first handle ring 330 so that shifting the second handle rings 332 relative to the first handle ring 330 shifts the net system 316 alternatively into and out of the introducer passage opening 312.

Introducer member passage or lumen 310 has a diametrical extent substantially smaller than the widths of cauterization snare 314 and net loop 318 when the snare and the loop are deployed. Introducer member 308 engages at least loop 318 at the opening 312 and resiliently collapses and elongates cauterization snare 314 and net loop 318 as snare and/or net is retracted and moves into the introducer member passage 310. Snare 314 and net loop 318 resiliently return to an uncollapsed or expanded configuration as net system is ejected and deployed.

Net system 316 further includes a net controller 334 (FIG. 9) for assuring that the net mouth 322 extends fully about loop 318 when the loop is deployed. Controller 334 comprises one or more net tethers 336 each having one end 338 anchored within the introducer member passage 310 a distance D1 from opening 312 at the distal tip of tubular introducer member 308. An opposite end 340 of each tether section 336 engages net element 320. More particularly, net element 320 includes a proximal section 342 that extends proximally of net mouth 322 and into introducer passage or lumen 310 in a fully extended or fully deployed state of net system 316. Tether sections 336 may be portions of a common tether thread that is connected to net element 320 at 344. Alternatively, ends 340 of tether sections 336 may be bonded or fixed to net thread 344. Each tether section 336 has a free length L1 that is less than the distance D1 between introducer member opening 312 and fixed tether ends 338. Tether or controller 334 assures a full opening of net mouth 322 when the net system 316 is deployed while permitting the mouth to be closed when tissue is disposed in the net pouch 324 and the loop 318 is retrieved.

FIG. 10 shows a cauterization loop 350 with a web member or net element 352 joined at three fixed positions by clamps 360 and 360' that secure three connecting strands 354 of the web member or net element to a distal end of the loop. Connecting strands 356 at the proximal end of the net element 352 are slidingly connected to cauterization loop 350 by ringlets 358, wound threads that are tied or joined at their free ends by spots of adhesive, etc. Permanent attachment of proximal sliding connecting strands 356 to loop 350 prevents separation of net element 352 from loop 350 during a transection procedure and provides additional assurance that the net element or capture pocket 352 will not become detached from loop 350 while inside the patient.

A proximal end portion 362 of net element 352 is located at all times within a tubular introducer member 364, particularly when loop 350 is fully extended from the tubular introducer member. Net end portion 362 is connected to a tether 366 that, like controller or tether 334, is connected to introducer member 364 inside a lumen thereof. Like controller or tether 334, tether 366 has a length that is less than the distance between the distance tip of tubular introducer member 364 and the point of attachment of tether 366 to the introducer member.

After electrical current is supplied to cauterization loop 350 to sever a tissue sample, the severed tissue sample is contained in the web capture pocket or net element 352. When loop 350 is withdrawn into tubular member 364, the sliding connecting strands 356 previously located at the proximal end of the loop are moved toward the distal end of the loop. As cautery is activated, the cautery snare becomes hot only when in contact with tissue. Thus, only the most distal aspect of the snare that engulfs tissue is heated. Any portion of the snare not in contact with tissue will not be heated. When the fixed connecting strands 354 (and any intervening strands positioned between side ringlets 360 and the most distal ringlet located on the nose or most distal tip of the snare) have been melted by the cauterization heat, the netting proximal to the two side ringlets is left intact because it is not exposed to tissue. A small gap at the very distal end of the pocket or net element 352 exists where the most distal strands were melted. However, because over 90% of the net remains intact, the sample will not become dislodged from its position inside the capture pocket. In addition, the specimen is wet and sticky, and is thereby held securely inside the netting. This embodiment is described in U.S. Pat. No. 5,782,840 (incorporated herein by reference).

The retrieval instrument of FIG. 11 does not cauterize. It can only retrieve (and cut in a guillotine or garroting, and in this case can retrieve larger or smaller specimens. As illustrated in FIG. 11 and as disclosed in U.S. Patent Publication No. 20050085808 (incorporated by reference herein), an endoscopic retrieval instrument comprises an elongate tubular member 412, a handle with a slidable actuator as shown in FIG. 6, and an inwardly dented loop 418 made of a wire or other stiff but resilient material as is well known in the art. Tubular member 412 is a catheter attached at its proximal end to the handle. Loop 418 is attached to a distal end of an elongate rod or wire member 420 extending longitudinally through tubular member 412 to the slidable actuator. A metal tip element in the form of a sleeve 419 is inserted in the distal end of tubular member 412 and is rigidly fastened thereto. Sleeve 419 is a serves as a guide for loop 418 during ejection and retraction procedures. To that end, sleeve 419 is provided at a free end with a segment 421 that is rectangular in cross-section. In a most distal position of the sliding actuator relative to the handle or grip, loop 418 is in a fully extended and fully opened configuration. In that configuration, loop 418 has a size adapted for severing a large polyp.

The endoscopic retrieval instrument of FIG. 11 further comprises a flexible basket or pouch 458 made of a netting material attached to loop 418 for enabling the retrieval of tissue masses of different sizes. With this instrument, several polyps of different sizes may be captured during the same endoscope deployment procedure, without the necessity for withdrawing the endoscope from the patient upon the severing and capture of each specimen.

As shown in FIG. 11, loop 418 is formed on a distal side with three bends 422, 423, 424 defining nose 426, which projects in the distal direction away from tubular member or catheter 412 and rod or wire member 420. Loop 418 further includes two mirror-image loop sections 428 and 430 each extending between elongate rod or wire member 420 and a respective bend 422 or 423 of nose 426.

Loop sections 428 and 430 are formed with respective V-shaped notches or dents 432 and 434 for enabling a use of the loop in a second, smaller size. In this smaller deployment configuration, loop 418 is suitable for the harvesting of a small polyp. More specifically, notches or dents 432 and 434 facilitate the use of a distal end portion 436 of loop 418 as a smaller, auxiliary loop, distal end portion 436 being bounded by the notches or dents on the proximal side and nose 26 on the distal side.

Notches or dents 432 and 434 are of a size and geometry to releasably catch on the mouth rim or lip of tubular member 412, thereby preventing loop 418 from sliding uncontrollably either in proximal or distal direction relative to tubular member 412.

A proximal end portion 462 of pouch or net element 458 is partially located at all times within tubular introducer catheter 412, particularly when loop 418 is fully extended from the tubular introducer catheter. Net end portion 462 is connected to a tether 466 that, like controller or tether 334, is connected to introducer member 418 inside a lumen thereof. Like controller or tether 334, tether 466 has a length that is less than the distance between the distance tip of tubular introducer catheter 412 and the point of attachment of tether 466 to the catheter.

Figure 12:
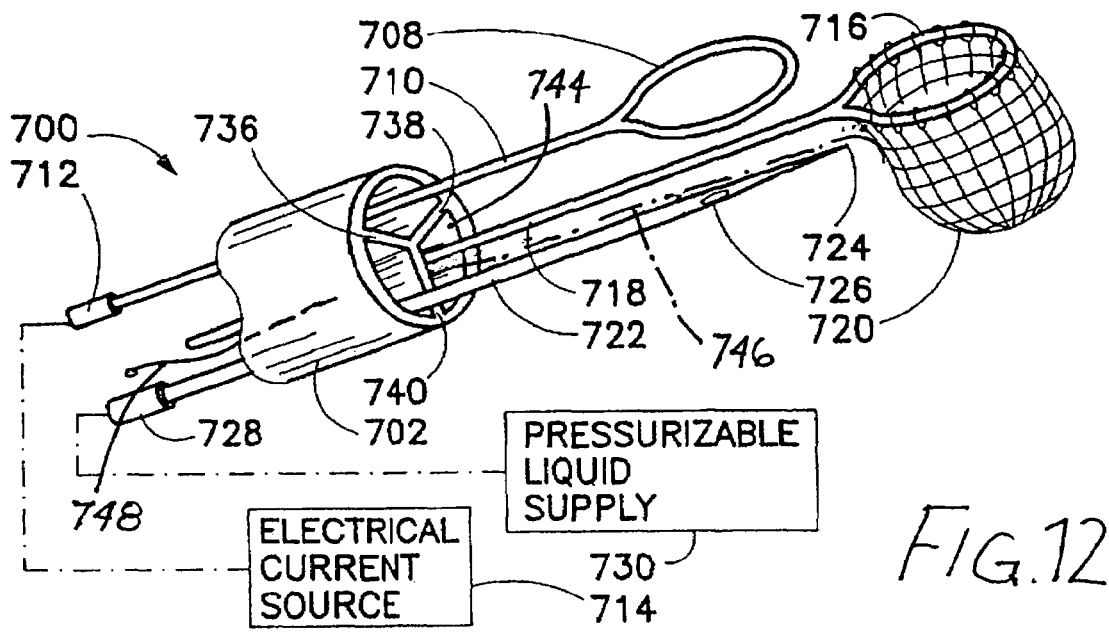
FIG. 12 is a partial schematic perspective view of an additional surgical retrieval device pursuant to principles of the present invention.

As shown in FIG. 12 and as disclosed in U.S. Pat. Nos. 5,741,271 and 5,997,547 (incorporated by reference herein), an endoscopic instrument assembly 700 for use in severing and retrieving a sessile or nonprojecting polyp from a wall of a colon or other internal organ comprises a tubular instrument guide or introducer member 702 having a diameter sufficiently small so that the tubular member can be inserted through a biopsy channel 704 of a flexible endoscope 706 (FIGS. 30A-30D). Assembly 700 includes a cauterization loop 708 and an electrically conductive wire 710 operatively connected to the cauterization loop, the cauterization loop and the wire being disposed at least partially in tubular member 702. An electrical connector 712 is operatively connected to wire 710 for feeding an electrical current from a current source 714 to cauterization loop 708 via the wire. Assembly 700 further includes an auxiliary loop 716 provided at a distal end of an elongate flexible shifting member 718. Auxiliary loop 716 and shifting member 718 are at least partially disposed in tubular member 702. A flexible web member 720 is connected to auxiliary loop 716 so as to form a capture pocket, the auxiliary loop defining a mouth opening of the pocket. Assembly 700 also includes an elongate flexible tube 722 provided at a distal end with a hollow needle point 724 and an aperture 726. Tube 722 is disposed at least partially in tubular member 702 and is provided at a proximal end with a fluid feed connector 728 for coupling the tube to a pressurizable liquid supply 730, whereby fluid is fed to tube 722 for ejection through aperture 726.

Web member or net element 720 is attached at a proximal end to a tether 742 that extends into a lumen 744 of instrument guide or introducer member 702 and is attached thereto inside lumen 744 Web member or net element 720 may be provided with a net portion 746 that extends from the distal end of the net proper into lumen 744 of instrument guide or introducer member 702. Net portion 746 is connected inside lumen 744 to one end of a tether 748 that is in turn connected to instrument guide or introducer member 702 inside lumen 744.

Figure 13:
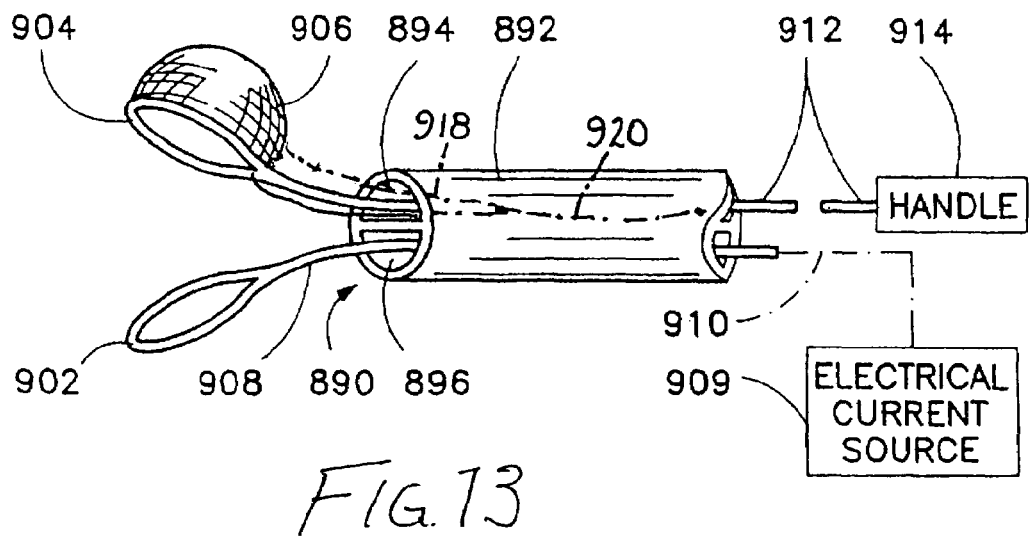
FIG. 13 is a partial schematic perspective view of yet another surgical retrieval device pursuant to principles of the present invention.

As shown in FIG. 13 and as disclosed in U.S. Pat. No. 5,759,187 (incorporated by reference herein), a surgical instrument assembly 890 for use in snare cauterization operations comprises a tubular instrument guide or introducer member 892 defining a plurality of separate longitudinally extending lumens 894 and 896. Lumens 894 and 896 have semi-circular cross-sections, but may have other configurations to accommodate for the netting material such as a sliver-moon shape and a circle. Tubular member 892 has a diameter sufficiently small so that the tubular member can be inserted through a biopsy channel 898 of a flexible endoscope insertion member 900. Instrument assembly 890 further comprises a cauterization loop 902 and an auxiliary loop 904 which is provided with a flexible web member 906 defining an alternately expandable and contractible capture pocket. Auxiliary loop 904 defines a mouth opening of the pocket.

An electrically conductive wire 908 is connected to cauterization loop 902, cauterization loop 902 and wire 908 being disposed at least partially in lumen 896 of tubular member 892. An electrical supply 909 is operatively connected to wire 908 via a coupling 910 for feeding an electrical current to cauterization loop 902 via wire 908. An elongate flexible shifting member 912 (e.g., a wire) is connected at one end to auxiliary loop 904. Auxiliary loop 904 and wire 912 are at least partially disposed in lumen 894 of tubular member 892. A handle assembly 914 is provided at the proximal end of wire 912 for facilitating the maneuvering of auxiliary loop 904 from outside the patient. Handle assembly 914 may also be connected to cauterization loop 902 to facilitate the manipulation of the loop to eject the loop from lumen 896 and to place the loop about a polyp. Handle assembly 914 is operatively connected to cauterization loop 902 and auxiliary loop 904 so as to allow those two elements to be ejected independently from tubular member or catheter 892.

Web member 906, whether a net element or a continuous film of polymeric material, may be connected to auxiliary loop 904 at a plurality of spaced locations, e.g., via ringlets (not shown). Tubular member 892 is preferably flexible so that it may pass along bends in endoscope insertion member 900 upon a deployment thereof during an endoscopic investigation.

Web member or net element 906 is attached at a proximal end to a tether 916 that extends into lumen 894 of instrument guide or introducer member 892 and is attached thereto inside lumen 894. Web member or net element 906 may be provided with a net portion 918 that extends from the distal end of the net proper into lumen 894 of instrument guide or introducer member 892. Net portion 918 is connected inside lumen 894 to one end of a tether 920 that is in turn connected to instrument guide or introducer member 892 inside lumen 894. Tether 920 serves to maintain web member or net element 906 in an opened configuration upon an ejection of loop 904 from lumen 894.

FIG. 14 illustrates a surgical retrieval device identical to that of FIG. 10, except that loop sections 428 and 430 are formed without V-shaped notches or dents 432 and 434 of the embodiment of FIG. 10. The retrieval device of FIG. 14 is thus a general purpose capture and entrainment device.

FIG. 15 depicts surgical retrieval device identical to that of FIG. 11 except that clamps 360 have been omitted.

Although the invention has been described in terms of particular embodiments and applications, one of ordinary skill in the art, in light of this teaching-, can generate additional embodiments and modifications without departing from the spirit of or exceeding the scope of the claimed invention. For instance, the cauterization snares described above may be modified to take the form of a monofilament wire or a thin braided cable that is used to cut small polyps by simply being drawn through base regions of the polyps. Such a thin wire or cable severs tissue via a "cold" cutting technique, rather than via a "hot" cauterization technique. Such a cold cutting technique is appropriate where a polyp is so small as to be vascularized by only capillaries, without a dedicated artery. Thus, loops 14 and 114, particularly the distal loop portions 20 and 120, snare 314, loop 350, loop 708, and loop 902 may take the form of monofilament snares in certain applications. Whether the snare is a cold-cutting snare or a cauterization snare, it serves in both cases to cut/resect a lesion.

Accordingly, it is to be understood that the drawings and descriptions herein are proffered by way of example to facilitate comprehension of the invention and should not be construed to limit the scope thereof.

What is claimed is:

1. A medical instrument comprising:
an elongate tubular member;
an elongate slider member disposed at least partially inside said tubular member;
a loop at a distal end of said slider member;
a pouch connected to said loop so that said loop defines a mouth opening of said pouch and so that said pouch is slidable along at least a proximal portion of said loop; and
at least one tether operatively connected to said pouch at a proximal side thereof, said tether extending into said tubular member,
said tether being fastened to said tubular member at a location spaced by a distance from a distal tip of said tubular member,
said tether having a length from said location to said pouch that is less than said distance between said location and said tip of said tubular member.

2. The medical instrument defined in claim 1 wherein said tubular member has a transverse dimension suitable for insertion of said instrument through a working channel of an endoscope.

3. The medical instrument defined in claim 1 wherein said loop is a monofilament cutting snare.

4. The medical instrument defined in claim 1 wherein said slider member is connectable at a proximal end to a source of electrical current, said loop being a cauterization snare made of a conductive material.

5. The medical instrument defined in claim 1 wherein said loop is a first loop, further comprising a second loop attached at least indirectly to said first loop on a proximal side thereof, said second loop being smaller than said first loop, said slider member being connectable at a proximal end to a source of electrical current, said second loop being made of a conductive material.

6. The medical instrument defined in claim 1 wherein said loop is a first loop, further comprising a second loop attached at least indirectly to said first loop on a proximal side thereof, said second loop being smaller than said first loop, said second loop being made at least in part of a monofilament wire.

7. The medical instrument defined in claim 1 wherein said pouch is a net, a distal portion of said tether being interwoven with said net.

8. The medical instrument defined in claim 1 wherein said pouch includes a proximal end portion that extends into said tubular member.

9. A medical instrument comprising:
an elongate tubular member;
an elongate slider member disposed at least partially inside said tubular member;
a first loop at a distal end of said slider member;
a second loop serving as a cutting snare, said second loop being smaller than and nestable inside said first loop, said second loop being deployed via said tubular member;
a pouch connected to said first loop so that said first loop defines a mouth opening of said pouch and so that said pouch is slidable along at least a proximal portion of said first loop; and
at least one tether operatively connected to said pouch at a proximal side thereof, said tether extending into said tubular member,
said tether being fastened to said tubular member at a location spaced by a distance from a distal tip of said tubular member,
said tether having a length from said location to said pouch that is less than said distance between said location and said tip of said tubular member.

10. The medical instrument defined in claim 9 wherein said first loop and said second loop are connected to one another and to said slider member only along stems at the proximal ends of the respective loops.

11. A medical instrument comprising:
an elongate tubular member;
an elongate slider member disposed at least partially inside said tubular member;
a first loop at a distal end of said slider member;
a second loop at a distal end of said slider member, said second loop serving as a cutting snare, said second loop being smaller than and nested inside said first loop, said first loop and said second loop sharing a common proximal portion and having separate distal portions;
a pouch connected to said first loop so that said first loop defines a mouth opening of said pouch and so that said pouch is slidable along at least a proximal portion of said first loop; and
at least one tether operatively connected to said pouch at a proximal side thereof, said tether extending into said tubular member,
said tether being fastened to said tubular member at a location spaced by a distance from a distal tip of said tubular member,
said tether having a length from said location to said pouch that is less than said distance between said location and said tip of said tubular member.

12. A medical instrument comprising:
an elongate tubular member provided with a plurality of lumens;
an elongate first slider member disposed at least partially inside a first of said lumens;
a first loop at a distal end of said first slider member;
an elongate second slider member disposed at least partially inside a second of said lumens;
a second loop at a distal end of said second slider member, said second loop serving as a cutting snare;
a pouch connected to said first loop so that said first loop defines a mouth opening of said pouch and so that said pouch is slidable along at least a proximal portion of said first loop; and
at least one tether operatively connected to said pouch at a proximal side thereof, said tether extending into said first of said lumens,
said tether being fastened to said tubular member at a location spaced by a distance from a distal tip of said tubular member,
said tether having a length from said location to said pouch that is less than said distance between said location and said tip of said tubular member.

13. A medical instrument comprising:
an elongate tubular member;
an elongate slider member disposed at least partially inside said tubular member;
a resilient loop of a first size attached to one end of said elongate member, said loop including a bend on a side of said loop opposite said elongate member, said loop further including two loop sections each extending between said elongate member and said bend, at least one of said loop sections being formed with at least one notch or dent for enabling a use of said loop in at least one second size smaller than said first size upon a positioning of said loop by moving said elongate member and said tubular member relative to one another so that said notch or dent is disposed at a mouth opening of said tubular member; and a pouch connected to said loop so that said loop defines a mouth opening of said pouch and so that said pouch is slidable along at least a proximal portion of said loop; and at least one tether operatively connected to said pouch at a proximal side thereof, said tether extending into said tubular member, said tether being fastened to said tubular member at a location spaced by a distance from a distal tip of said tubular member, said tether having a length from said location to said pouch that is less than said distance between said location and said tip of said tubular member.

14. A medical instrument comprising:

an elongate tubular member;

an elongate slider member disposed at least partially inside said tubular member;

a cutting loop at a distal end of said slider member;

a pouch connected to said loop so that said loop defines a mouth opening of said pouch and so that said pouch is slidable along at least a proximal portion of said loop; and at least one tether operatively connected to said pouch at a proximal side thereof, said tether extending into said tubular member, said tether being fastened to said tubular member at a location spaced by a distance from a distal tip of said tubular member, said tether having a length from said location to said pouch that is less than said distance between said location and said tip of said tubular member, said pouch being fixed to said loop at a distal end thereof by at least at one point.

15. A medical instrument comprising:

an elongate tubular member;

an elongate slider member disposed at least partially inside said tubular member;

a loop at a distal end of said slider member;

a pouch connected to said loop so that said loop defines a mouth opening of said pouch and so that said pouch is slidable along at least a proximal portion of said loop; and at least one tether operatively connected to said pouch at a proximal side thereof, said tether extending into said tubular member, said tether being fastened to said tubular member at a location spaced by a distance from a distal tip of said tubular member, said tether having a length from said location to said pouch that is less than said distance between said location and said tip of said tubular member, said pouch being fixed to said loop at a distal end thereof at least in one point.

* * * * *

UNITED STATES PATENT AND TRADEMARK OFFICE
CERTIFICATE OF CORRECTION

PATENT NO. : 7,618,437 B2  Page 1 of 1
APPLICATION NO. : 11/182404
DATED : November 17, 2009
INVENTOR(S) : Naomi L. Nakao It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this

Twenty-sixth Day of October, 2010

David J. Kappos
*Director of the United States Patent and Trademark Office*